(12) United States Patent
Peine (10) Patent No.: US 11,628,022 B2
(45) Date of Patent: Apr. 18, 2023

(54) COLLISION HANDLING ALGORITHMS FOR ROBOTIC SURGICAL SYSTEMS

(71) Applicant: Covidien LP, Mansfield, MA (US)

(72) Inventor: William Peine, Ashland, MA (US)

(73) Assignee: Covidien LP, Mansfield, MA (US)

( * ) Notice: Subject to any disclaimer, the term of this patent is extended or adjusted under 35 U.S.C. 154(b) by 460 days.

(21) Appl. No.: 16/643,306

(22) PCT Filed: Sep. 4, 2018

(86) PCT No.: PCT/US2018/049334
§ 371 (c)(1),
(2) Date: Feb. 28, 2020

(87) PCT Pub. No.: WO2019/050829
PCT Pub. Date: Mar. 14, 2019

(65) Prior Publication Data
US 2020/0345433 A1  Nov. 5, 2020

Related U.S. Application Data (60) Provisional application No. 62/554,331, filed on Sep. 5, 2017.

(51) Int. Cl.
*A61B 34/30* (2016.01)
*A61B 34/00* (2016.01)
*B25J 9/16* (2006.01)

(52) U.S. Cl.
CPC .............. *A61B 34/30* (2016.02); *A61B 34/76* (2016.02); *B25J 9/1633* (2013.01); *B25J 9/1674* (2013.01); *A61B 2034/742* (2016.02)

(58) Field of Classification Search
CPC ... A61B 34/30; A61B 34/76; A61B 2034/742; A61B 2090/065; A61B 34/37;
(Continued)

(56) References Cited

U.S. PATENT DOCUMENTS

| 6,132,368 A | 10/2000 | Cooper |
| 6,206,903 B1 | 3/2001 | Ramans |

(Continued)

FOREIGN PATENT DOCUMENTS

| EP | 1871267 A1 | 1/2008 |
| JP | 2009240789 A | 10/2009 |

(Continued)

OTHER PUBLICATIONS

Extended European Search Report dated Aug. 27, 2021 corresponding to counterpart Patent Application EP18853152.9.
(Continued)

*Primary Examiner* — Robert T Nguyen
(74) *Attorney, Agent, or Firm* — Carter, DeLuca & Farrell LLP (57) ABSTRACT

Methods of collision handling for robotic surgical systems include slipping an input handle of a user interface of the robotic surgical system relative to a pose of a tool of a surgical robot of the robotic surgical system when a portion of the surgical robot collides with an obstruction and an input handle is moved in a direction that corresponds to moving the tool towards the obstruction. The input handle having an offset relative to a desired pose of the tool after the input handle is slipped.

20 Claims, 4 Drawing Sheets

(58) Field of Classification Search
CPC ........ A61B 34/74; A61B 34/77; B25J 9/1633; B25J 9/1674; B25J 9/1676; B25J 9/1612
See application file for complete search history.

(56) References Cited

U.S. PATENT DOCUMENTS

| | | |
|---|---|---|
| 6,246,200 B1 | 6/2001 | Blumenkranz et al. |
| 6,312,435 B1 | 11/2001 | Wallace et al. |
| 6,331,181 B1 | 12/2001 | Tierney et al. |
| 6,394,998 B1 | 5/2002 | Wallace et al. |
| 6,424,885 B1 | 7/2002 | Niemeyer et al. |
| 6,441,577 B2 | 8/2002 | Blumenkranz et al. |
| 6,459,926 B1 | 10/2002 | Nowlin et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,565,554 B1 | 5/2003 | Niemeyer |
| 6,645,196 B1 | 11/2003 | Nixon et al. |
| 6,659,939 B2 | 12/2003 | Moll et al. |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,035,716 B2 | 4/2006 | Harris et al. |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,155,316 B2 | 12/2006 | Sutherland et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco et al. |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez et al. |
| 8,004,229 B2 | 8/2011 | Nowlin et al. |
| 8,010,180 B2 | 8/2011 | Quaid et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,083,691 B2 | 12/2011 | Goldenberg et al. |
| 8,092,397 B2 | 1/2012 | Wallace et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |

(56) References Cited

U.S. PATENT DOCUMENTS

| | | |
|---|---|---|
| 8,749,190 B2 | 6/2014 | Nowlin et al. |
| 8,753,346 B2 | 6/2014 | Suarez et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,828,023 B2 | 9/2014 | Neff et al. |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart et al. |
| 8,989,903 B2 | 3/2015 | Weir et al. |
| 9,002,518 B2 | 4/2015 | Manzo et al. |
| 9,014,856 B2 | 4/2015 | Manzo et al. |
| 9,016,540 B2 | 4/2015 | Whitman et al. |
| 9,019,345 B2 | 4/2015 | Patrick |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,266,239 B2 * | 2/2016 | Miller .................. A61B 90/37 |
| 9,283,049 B2 | 3/2016 | Diolaiti et al. |
| 9,301,811 B2 | 4/2016 | Goldberg et al. |
| 9,308,646 B2 | 4/2016 | Lim et al. |
| 9,314,307 B2 | 4/2016 | Richmond et al. |
| 9,317,651 B2 | 4/2016 | Nixon |
| 9,333,650 B2 | 5/2016 | Bajo et al. |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti et al. |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,469,034 B2 | 10/2016 | Diolaiti et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,687,312 B2 | 6/2017 | Dachs, II et al. |
| 9,696,700 B2 | 7/2017 | Beira et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin et al. |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |

(56) References Cited

U.S. PATENT DOCUMENTS

| | | |
|---|---|---|
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 10,939,969 B2 | 3/2021 | Swarup et al. |
| 10,939,973 B2 | 3/2021 | DiMaio et al. |
| 10,952,801 B2 | 3/2021 | Miller et al. |
| 10,965,933 B2 | 3/2021 | Jarc |
| 10,966,742 B2 | 4/2021 | Rosa et al. |
| 10,973,517 B2 | 4/2021 | Wixey |
| 10,973,519 B2 | 4/2021 | Weir et al. |
| 10,984,567 B2 | 4/2021 | Itkowitz et al. |
| 10,993,773 B2 | 5/2021 | Cooper et al. |
| 10,993,775 B2 | 5/2021 | Cooper et al. |
| 11,000,331 B2 | 5/2021 | Krom et al. |
| 11,013,567 B2 | 5/2021 | Wu et al. |
| 11,020,138 B2 | 6/2021 | Ragosta |
| 11,020,191 B2 | 6/2021 | Diolaiti et al. |
| 11,020,193 B2 | 6/2021 | Wixey et al. |
| 11,026,755 B2 | 6/2021 | Weir et al. |
| 11,026,759 B2 | 6/2021 | Donlon et al. |
| 11,040,189 B2 | 6/2021 | Vaders et al. |
| 11,045,077 B2 | 6/2021 | Stem et al. |
| 11,045,274 B2 | 6/2021 | Dachs, II et al. |
| 11,058,501 B2 | 7/2021 | Tokarchuk et al. |
| 11,076,925 B2 | 8/2021 | DiMaio et al. |
| 11,090,119 B2 | 8/2021 | Burbank |
| 11,096,687 B2 | 8/2021 | Flanagan et al. |
| 11,098,803 B2 | 8/2021 | Duque et al. |
| 11,109,925 B2 | 9/2021 | Cooper et al. |
| 11,116,578 B2 | 9/2021 | Hoffman et al. |
| 11,129,683 B2 | 9/2021 | Steger et al. |
| 11,135,029 B2 | 10/2021 | Suresh et al. |
| 11,147,552 B2 | 10/2021 | Burbank et al. |
| 11,147,640 B2 | 10/2021 | Jarc et al. |
| 11,154,373 B2 | 10/2021 | Abbott et al. |
| 11,154,374 B2 | 10/2021 | Hanuschik et al. |
| 11,160,622 B2 | 11/2021 | Goldberg et al. |
| 11,160,625 B2 | 11/2021 | Wixey et al. |
| 11,161,243 B2 | 11/2021 | Rabindran et al. |
| 11,166,758 B2 | 11/2021 | Mohr et al. |
| 11,166,770 B2 | 11/2021 | DiMaio et al. |
| 11,166,773 B2 | 11/2021 | Ragosta et al. |
| 11,173,597 B2 | 11/2021 | Rabindran et al. |
| 11,185,378 B2 | 11/2021 | Weir et al. |
| 11,191,596 B2 | 12/2021 | Thompson et al. |
| 11,197,729 B2 | 12/2021 | Thompson et al. |
| 11,213,360 B2 | 1/2022 | Hourtash et al. |
| 11,221,863 B2 | 1/2022 | Azizian et al. |
| 11,234,700 B2 | 2/2022 | Ragosta et al. |
| 11,241,274 B2 | 2/2022 | Vaders et al. |
| 11,241,290 B2 | 2/2022 | Waterbury et al. |
| 11,259,870 B2 | 3/2022 | DiMaio et al. |
| 11,259,884 B2 | 3/2022 | Burbank |
| 11,272,993 B2 | 3/2022 | Gomez et al. |
| 11,272,994 B2 | 3/2022 | Saraliev et al. |
| 11,291,442 B2 | 4/2022 | Wixey et al. |
| 11,291,513 B2 | 4/2022 | Manzo et al. |
| 11,334,063 B2 * | 5/2022 | Celia .............. G05B 19/41865 |
| 2009/0076476 A1 | 3/2009 | Barbagli et al. |
| 2011/0015649 A1 | 1/2011 | Anvari et al. |
| 2011/0105898 A1 | 5/2011 | Guthart et al. |
| 2011/0319910 A1 | 12/2011 | Roelle et al. |
| 2012/0209069 A1 | 8/2012 | Popovic et al. |
| 2013/0090763 A1 | 4/2013 | Simaan et al. |
| 2014/0052150 A1 | 2/2014 | Taylor et al. |
| 2014/0058406 A1 | 2/2014 | Tsekos |
| 2014/0058564 A1 | 2/2014 | Zhao et al. |
| 2014/0228631 A1 | 8/2014 | Kwak et al. |
| 2015/0182285 A1 | 7/2015 | Yen et al. |
| 2015/0250547 A1 | 9/2015 | Fukushima et al. |
| 2015/0320514 A1 | 11/2015 | Ahn et al. |
| 2017/0112582 A1 | 4/2017 | Itkowitz et al. |
| 2017/0224428 A1 | 8/2017 | Kopp |
| 2018/0014897 A1 | 1/2018 | Peine |
| 2018/0310999 A1 | 11/2018 | Peine |
| 2020/0367984 A1 * | 11/2020 | Peine .................. B25J 9/1666 |

FOREIGN PATENT DOCUMENTS

| | | |
|---|---|---|
| JP | 5754820 B2 | 7/2015 |
| WO | 2014151550 A2 | 9/2014 |
| WO | 2016030336 A1 | 3/2016 |
| WO | 2016205266 A1 | 12/2016 |

OTHER PUBLICATIONS

International Search Report dated Dec. 19, 2018 and Written Opinion completed Dec. 19, 2018 corresponding to counterpart Int'l Patent Application PCT/US2018/049330.

Japanese Office Action dated Aug. 31, 2022 corresponding to counterpart Patent Application JP 2020-534809.

Indian Office Action dated Mar. 25, 2022 corresponding to counterpart Patent Application IN 202017008950.

* cited by examiner

COLLISION HANDLING ALGORITHMS FOR ROBOTIC SURGICAL SYSTEMS

CROSS-REFERENCE TO RELATED APPLICATIONS

This application is a U.S. National Stage Application filed under 35 U.S.C. § 371(a) of International Patent Application Serial No. PCT/US2018/049334, filed Sep. 4, 2018, which claims the benefit of and priority to U.S. Provisional Patent Application Ser. No. 62/554,331, filed Sep. 5, 2017, the entire disclosure of which is incorporated by reference herein.

BACKGROUND

Robotic surgical systems have been used in minimally invasive medical procedures. During a medical procedure, the robotic surgical system is controlled by a surgeon interfacing with a user interface. The user interface allows the surgeon to manipulate an end effector that acts on a patient.

The end effector is inserted into a small incision (via a cannula) or a natural orifice of a patient to position the end effector at a work site within the body of the patient. Some robotic surgical systems include a robotic console supporting a robot arm, and at least one end effector such as a scalpel, a forceps, or a grasping tool that is mounted to the robot arm.

In general, the user interface includes an input controller or handle that is moveable by the surgeon to control the robotic surgical system. Robotic surgical systems typically use a scaling factor to scale down the motions of the surgeons hands to determine the desired position of the robotic instruments within the patient. Often this scaling factor requires the motions of the handles to be larger than the range of motion of the input handle. The handles therefore reach a boundary limit of the workspace and prevent the surgeon from completing the desired motion. Current robotic surgical systems on the market use a feature called "clutching" to decouple the motion of the input handles from the robotic instruments. The surgeon is then free to move the handles to a new position within the workspace of the user interface while the instruments remain stationary. Once the input handle is away from the workspace boundary, the surgeon can "reclutch" to recouple the motion of the input handle to complete the desired motion with the robotic instrument.

During a robotic surgical procedure, the robot arm or end effector may collide with tissue, an organ, or another surgical implement (e.g., another robot arm or end effector, access port, or camera). Such collisions can create a positional mismatch between the position of the input handles and the robot arm or end effector associated with the input handle. This positional mismatch can create undesired motions of the robot arm or the end effector during the surgical procedure.

Accordingly, there is a need for collision handling algorithms for robotic surgical system.

SUMMARY

In an aspect of the present disclosure, a method of collision handling for a robotic surgical system includes slipping an input handle of a user interface of the robotic surgical system relative to a pose of a tool of a surgical robot of the robotic surgical system when a portion of the surgical robot collides with an obstruction and an input handle is moved in a direction that corresponds to moving the tool towards the obstruction. The input handle having an offset relative to a desired pose of the tool after the input handle is slipped.

In aspects, the method includes moving the input handle in a direction to move the portion of the surgical robot away from the obstruction after the slipping of the input handle. The input handle may move a distance corresponding to the offset before the tool moves in a direction away from the obstruction. Alternatively, the tool may move in a direction away from the obstruction while maintaining a trim between a position of the input handle and a pose of the tool. The trim may be equal to the offset or the method may include dynamically scaling movement of the input handle relative to the pose of the tool in a direction parallel to the offset until the trim reaches a predetermined value. The predetermined value may be zero or nonzero.

In some aspects, slipping the handle relative to the pose of the tool occurs after the surgical robot reaches the predetermined force threshold to move the tool towards a desired pose. The method may further include a processing unit of the robotic surgical system to define the offset between a threshold position of the input handle when the tool reaches the predetermined force threshold and a position of the input handle after the input handle is pushed beyond the threshold position. The method may include the robotic surgical system providing force feedback to a clinician to resist slipping of the input handle beyond the threshold position.

In another aspect of the present disclosure, a method of collision handling of a robotic surgical system with a processing unit of the robotic surgical system includes receiving a first input signal from a user interface of the robotic surgical system to move a tool of a surgical robot of the robotic surgical system to a desired pose of the tool, transmitting an input control signal to the surgical robot to move the tool towards the desired pose, receiving a feedback signal from the surgical robot that a force to move the tool towards the desired pose is greater than a predetermined threshold, maintaining the tool at a threshold pose when the predetermined threshold is reached, and slipping a position of the input handle relative to the threshold pose to a second position of the input handle to define an offset between the second position of the input handle and a desired pose of the tool corresponding to the second position of the input handle.

In aspects, the method includes transmitting a feedback control signal to the user interface to resist movement of the input handle beyond a threshold position corresponding to the threshold pose of the tool.

In some aspects, the method includes receiving a second input signal from the user interface after slipping the position of the input handle indicative of the input handle moving towards a threshold position corresponding to the threshold pose of the tool. The method may include maintaining the tool in the threshold pose in responds to receiving the second input signal. Alternatively, the method may include transmitting a second control signal to the surgical robot to move the tool away from the desired pose with a trim defined between the input handle and the pose of the tool. Transmitting the second control signal may include the trim being equal to the offset between the second position of the input handle and the desired pose of the tool corresponding to the second position of the input handle. The method may include dynamically scaling movement of the input handle to the pose of the tool to reduce the trim between the position of the input handle and the pose of the tool until the trim reaches a predetermined value. The predetermined value may be zero or nonzero.

Further details and aspects of exemplary embodiments of the present disclosure are described in more detail below with reference to the appended figures.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician. In addition, as used herein the term "neutral" is understood to mean non-scaled.

This disclosure generally relates to collision handling and collision recovery algorithms or methods for robotic surgical systems. Specifically, for collision handling a processing unit of a robotic surgical system may allow an input handle of a user interface to slip beyond a position corresponding to a pose of a tool of a surgical robot when a portion of the surgical robot collides with an obstruction. Slipping the input handle relative to the pose of the tool defines an offset between the position of the input handle and a pose of the tool.

To recover from the collision, the input handle may move through the entire offset before the tool moves from the pose when the surgical robot collided with the obstruction. Alternatively, any movement of the input handle to move the surgical robot away from the obstruction would move the surgical robot away from the obstruction such that a trim is defined between the position of the input handle and a pose of the tool. The trim may be equal to the offset or the robot surgical system may dynamically scale movement of the surgical robot to reduce or remove the trim in a manner imperceptible to a clinician.

Figure 1:
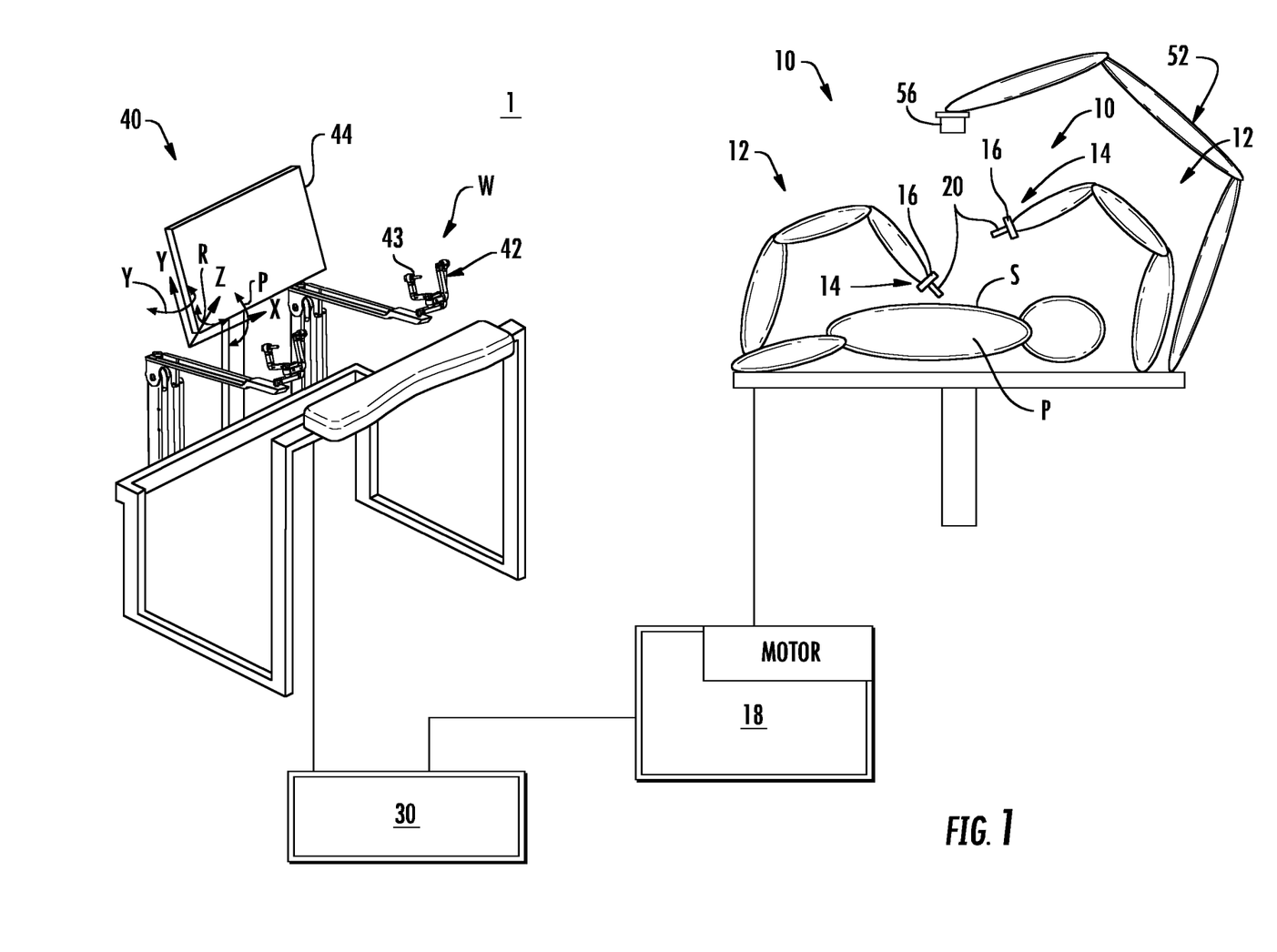
FIG. 1 is a schematic illustration of a user interface and a robotic system in accordance with the present disclosure.

Referring to FIG. 1, a robotic surgical system 1 in accordance with the present disclosure is shown generally as a surgical robot 10, a processing unit 30, and a user interface 40. The surgical robot 10 generally includes linkages 12 and a robot base 18. The linkages 12 moveably support an end effector or tool 20 which is configured to act on tissue. The linkages 12 may be in the form of arms each having an end 14 that supports an end effector or tool 20 which is configured to act on tissue. In addition, the ends 14 of the linkages 12 may include an imaging device 16 for imaging a surgical site "S". The user interface 40 is in communication with robot base 18 through the processing unit 30.

The user interface 40 includes a display device 44 which is configured to display three-dimensional images. The display device 44 displays three-dimensional images of the surgical site "S" which may include data captured by imaging devices 16 positioned on the ends 14 of the linkages 12 and/or include data captured by imaging devices that are positioned about the surgical theater (e.g., an imaging device positioned within the surgical site "S", an imaging device positioned adjacent the patient "P", imaging device 56 positioned at a distal end of an imaging arm 52). The imaging devices (e.g., imaging devices 16, 56) may capture visual images, infra-red images, ultrasound images, X-ray images, thermal images, and/or any other known real-time images of the surgical site "S". The imaging devices transmit captured imaging data to the processing unit 30 which creates three-dimensional images of the surgical site "S" in real-time from the imaging data and transmits the three-dimensional images to the display device 44 for display.

The user interface 40 also includes input handles 42 which are supported on control arms 43 which allow a clinician to manipulate the surgical robot 10 (e.g., move the arms 12, the ends 14 of the linkages 12, and/or the tools 20). Each of the input handles 42 is in communication with the processing unit 30 to transmit control signals thereto and to receive feedback signals therefrom. Additionally or alternatively, each of the input handles 42 may include input devices 46 (FIG. 2) which allow the surgeon to manipulate (e.g., clamp, grasp, fire, open, close, rotate, thrust, slice, etc.) the tools 20 supported at the ends 14 of the linkages 12.

Figure 2:
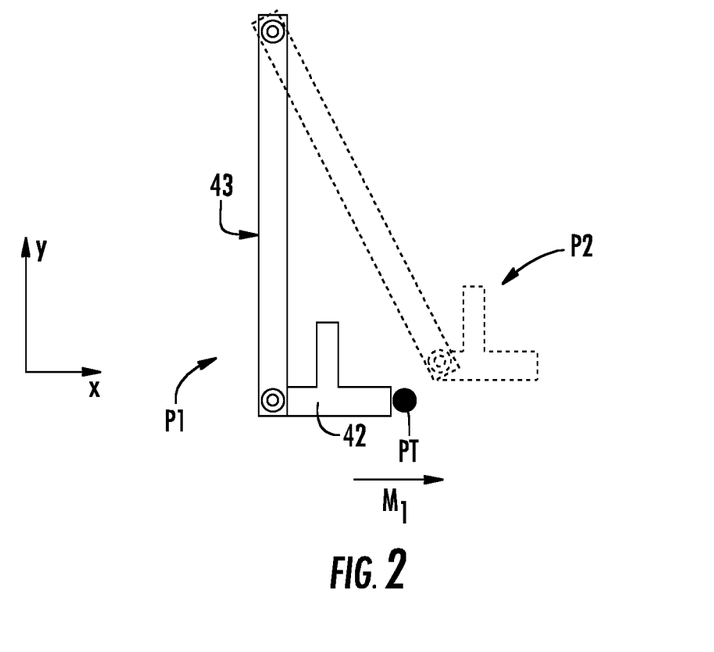
FIG. 2 is a plan view, schematic illustration, of a workspace of the user interface of FIG. 1.

With additional reference to FIG. 2, each of the input handles 42 is moveable through a predefined workspace to move the ends 14 of the linkages 12, e.g., tools 20 (FIG. 1), within a surgical site "S". The three-dimensional images on the display device 44 are orientated such that the movement of the input handles 42 moves the ends 14 of the linkages 12 as viewed on the display device 44. The three-dimensional images remain stationary while movement of the input handles 42 is scaled to movement of the ends 14 of the linkages 12 within the three-dimensional images. To maintain an orientation of the three-dimensional images, kinematic mapping of the input handles 42 is based on a camera orientation relative to an orientation of the ends 14 of the linkages 12. The orientation of the three-dimensional images on the display device 44 may be mirrored or rotated relative to view from above the patient "P". In addition, the size of the three-dimensional images on the display device 44 may be scaled to be larger or smaller than the actual structures of the surgical site permitting a clinician to have a better view of structures within the surgical site "S". As the input handles 42 are moved, the tools 20 are moved within the surgical site "S" as detailed below. Movement of the tools 20 may also include movement of the ends 14 of the linkages 12 which support the tools 20.

For a detailed discussion of the construction and operation of a robotic surgical system 1, reference may be made to U.S. Pat. No. 8,828,023, the entire contents of which are incorporated herein by reference.

The movement of the tools 20 is scaled relative to the movement of the input handles 42. When the input handles 42 are moved within a predefined workspace, the input handles 42 send input signals to the processing unit 30. The processing unit 30 analyzes the input signals to move the tools 20 in response to the input signals. The processing unit 30 transmits scaled control signals to the robot base 18 to move the tools 20 in response to the movement of the input handles 42. The processing unit 30 scales the input signals by dividing an Input$_{distance}$ (e.g., the distance moved by one of the input handles 42) by a scaling factor $S_F$ to arrive at a scaled Output$_{distance}$ (e.g., the distance that one of the ends 14 is moved). The scaling factor $S_F$ is in a range between about 1 and about 10 (e.g., 3). This scaling is represented by the following equation:

$$Output_{distance} = Input_{distance}/S_F$$

It will be appreciated that the larger the scaling factor $S_F$ the smaller the movement of the tools 20 relative to the movement of the input handles 42.

For a detailed description of scaling movement of the input handle 42 along the X, Y, and Z coordinate axes to movement of the tool 20, reference may be made to commonly owned International Patent Application Serial No. PCT/US2015/051130, filed Sep. 21, 2015, and International Patent Application No. PCT/US2016/14031, filed Jan. 20, 2016, the entire contents of each of these disclosures are herein incorporated by reference.

Figure 3:
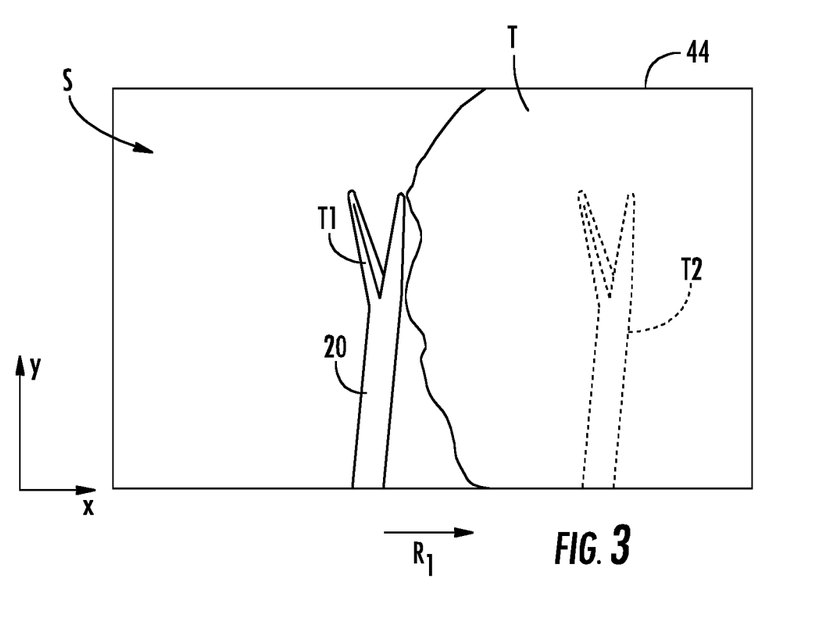
FIG. 3 is a view of a display device of the user interface of FIG. 1 illustrating a tool of a surgical robot within a surgical site.

Referring to FIGS. 1-3, during a robotic surgical procedure, a clinician interfaces with the input handle 42 to manipulate the tool 20 within the surgical site "S". As the tool 20 is moved within the surgical site "S", a clinician can visualize movement of the tool 20 within the surgical site "S" on the display 44.

To manipulate the tool 20, a clinician moves an input handle 42 from a first position "P1" to a second position "P2", shown in dashed lines (FIG. 2). The processing unit 30 receives an input signal sent from the user interface 40 and transmits a control signal to the surgical robot 10 to move the tool 20 from a first pose to a second pose. For example, the input handle 42 is moved a distance along a control X axis in a direction illustrated by arrow "M1" and the tool 20 is moved in a direction along a robotic X axis illustrated by arrow "R1" representing movement of the tool 20 from a first pose "T1" towards a second pose "T2".

During movement of the tool 20 from the first pose "T1" towards the second pose "T2", the tool 20 may collide with an obstruction within the surgical site "S", e.g., tissue T, another tool 20, an organ, or other surgical implement. When the tool 20 collides with the obstruction, the processing unit 30 receives a feedback signal from the surgical robot 10 and transmits a feedback control signal to the user interface 40. In response to receiving the feedback control signal, the user interface provides force feedback to the clinician indicative of the tool 20 colliding with the obstruction. For example, the clinician may feel resistance to continued movement along the control X axis in the direction of the arrow "M1".

When the clinician feels the force feedback, the clinician may push the input handle 42 against the force feedback (e.g., in a direction opposite to the direction of the force feedback) and continue to move the input handle 20 along the control X axis in the direction of arrow "M1". In response, the processing unit 30 continues to send control signals to the surgical robot 10 to move the tool 20 along the robotic X axis in the direction of arrow "R1" until the force of the surgical robot 10, to continue movement of the tool 20 along the robotic X axis, exceeds a predetermined threshold. The predetermined threshold may be determined by a deflection of a portion of the surgical robot 10 or by a torque at one or more joints of the surgical robot 10. When the force of the surgical robot 10 exceeds the predetermined threshold, the surgical robot 10 "clutches" the movement of the input handle 42 from movement of the robotic system 10, scales down movement of the input handle 42 from movement of the surgical robot 10, and/or any other known means of collision handling. For a detailed discussion of systems and methods for detecting and handling of a collision of a tool or linkage of a robotic system and an obstruction reference may be made to U.S. Provisional Patent Application Ser. No. XX/XXX,XXX, filed XXXX, and entitled "SURGICAL ROBOT INCLUDING TORQUE SENSORS, the entire contents of which are hereby incorporated by reference.

With particular reference to FIG. 2, the force to move the tool 20 along the robotic X axis was reached the predetermined threshold when the input handle 42 was positioned at a threshold position "PT". As shown, the input handle 42 was pushed through the threshold position "PT" to the second position "P2". As the input handle 42 is moved between the threshold position "PT" and the second position "P2" the tool 20 is substantially stationary within the surgical site "S", e.g., the tool 20 remains in the first pose "T1" as shown in FIG. 3, such that the input handle 42 "slips" relative to the tool 20. This "slipping" of the input handle 42 relative to the tool 20 results in a position mismatch between a desired pose "T2" of the tool 20 based on the position of the input handle 42 and the actual pose of the tool 20 which remains at the first pose "T1".

With the input handle 42 in the second position "P2", the surgical robot 10 maintains the tool 20 at the first pose "T1", the pose at which the predetermined threshold was reached, until the input handle 42 is moved along the control X axis in a direction that requires a force below the predetermined threshold to reposition the tool 20 along the robotic X axis, e.g., in a direction opposite the arrow "R1".

This position mismatch can create undesired motions of the tool 20 within the surgical site "S" during a surgical procedure. For example, when the input handle 42 is in the second position "P2", the tool 20 may be maintained in the first pose "T1" with the predetermined threshold force being directed towards an obstruction, e.g., tissue "T", such that, were the tool 20 to free itself from the obstruction, the tool 20 may move towards desired pose "T2" unexpectedly and/or at an undesired high velocity.

Figure 4:
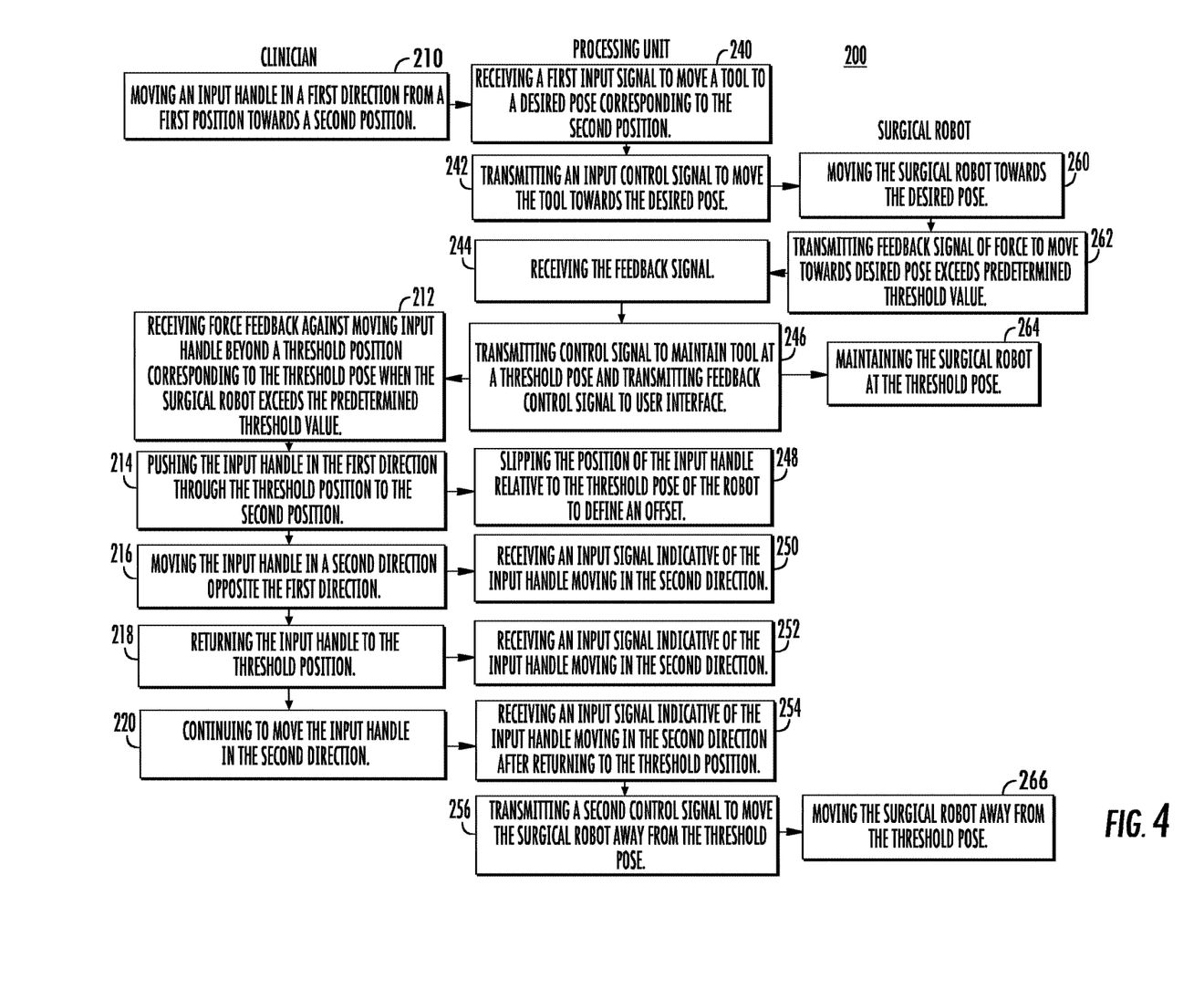
FIG. 4 is a flowchart of a method of collision handling and collision recovery in accordance with the present disclosure.

With reference to FIG. 4, a method 200 for slipping the input handle 42 relative to the tool 20 in an event of a collision with an obstruction and a method for collision recovery is disclosed, in accordance with the present disclosure, with reference to the robotic surgical system 1 of FIGS. 1-3. As detailed below, a collision between a tool 20 and tissue "T" of a patient is described; however, such a collision may be between any portion of the surgical robot 10 and an obstruction. For example, a collision may occur between a linkage 12 of the surgical robot 10 and another linkage 12.

Initially, a clinician moves the input handle 42 in a first direction along the control X axis towards the second position "P2" and transmits an input signal indicative of the movement (Step 210). The processing unit 30 receives the input signal (Step 240) and transmits an input control signal to move the tool 20 towards the desired pose of the surgical robot 10 (Step 242). The surgical robot 10 receives the control signal and moves the tool 20, and thus the surgical robot 10, towards the desired pose "T2" (Step 260).

As the tool 20 is moved towards the desired pose "T2", a portion of the surgical robot 10, e.g., tool 20, may collide with tissue "T" such that the surgical robot 10 would require a force greater than a predetermined threshold to continue to move the surgical robot 10 towards the desired pose "T2" (Step 262); this pose is defined as the threshold pose "T1". When the predetermined threshold is reached or exceeded, the surgical robot 10 transmits a feedback signal to the processing unit 30.

The processing unit 30 receives the feedback signal (Step 244) from the surgical robot 10 and transmits a control signal to the surgical robot 10 (Step 246) to maintain the surgical robot at the threshold pose "T1" (Step 264). In addition, the processing unit 30 transmits a feedback control signal to the user interface 40 (Step 246). In response to the feedback control signal, a clinician experiences force feedback against moving the input handle beyond a threshold position "PT" that corresponds to the threshold pose "T1" of the surgical robot 10 (Step 212).

The clinician may push the input handle 42 in the first direction through the force feedback of the user interface 40 to a second position "P2" (Step 214). The processing unit 30 receives an input signal in response to movement of the input handle 42 in the first direction and slips the position of the input handle 42 relative to the pose of the surgical robot 10 (Step 248). As the input handle 42 is moved beyond the threshold position "PT" an offset is generated along the control X axis as the input handle 42 is "slipped" between the threshold position "PT" and the second position "P2". The offset represents movement of the input handle 42 beyond the point at which the position of the input handle 42 corresponds to the pose of the surgical robot 10, e.g., the threshold position "PT", and the position of the input handle 42, e.g., the second position "P2".

With the input handle 42 at the second position "P2", the input handle 42 can be moved along the control X axis in a second direction away from the obstruction, e.g., the direction opposite the arrow "M1", (Step 216) such that the input handle 42 moves through a dead zone equal to the offset between the second position "P2" and the threshold position "PT" before the tool 20 of the surgical robot 10 moves along the robot X axis in a direction opposite the arrow "R1". Once the input handle 42 returns to the threshold position "PT" along the control X axis, the surgical robot 10 is recovered from the collision such that the surgical robot 10 moves the tool 20 along the robot X axis in response to additional movement of the input handle 42 in the second direction (Steps 220, 254, 256, 266). It will be appreciated that movement of the input handle 42 along the control X axis towards the threshold position "PT" will be allowed with little or no resistance, e.g., force feedback, while additional movement of the input handle 42 along the control X axis away from the threshold position "PT" will be resisted with additional force feedback.

Figure 5:
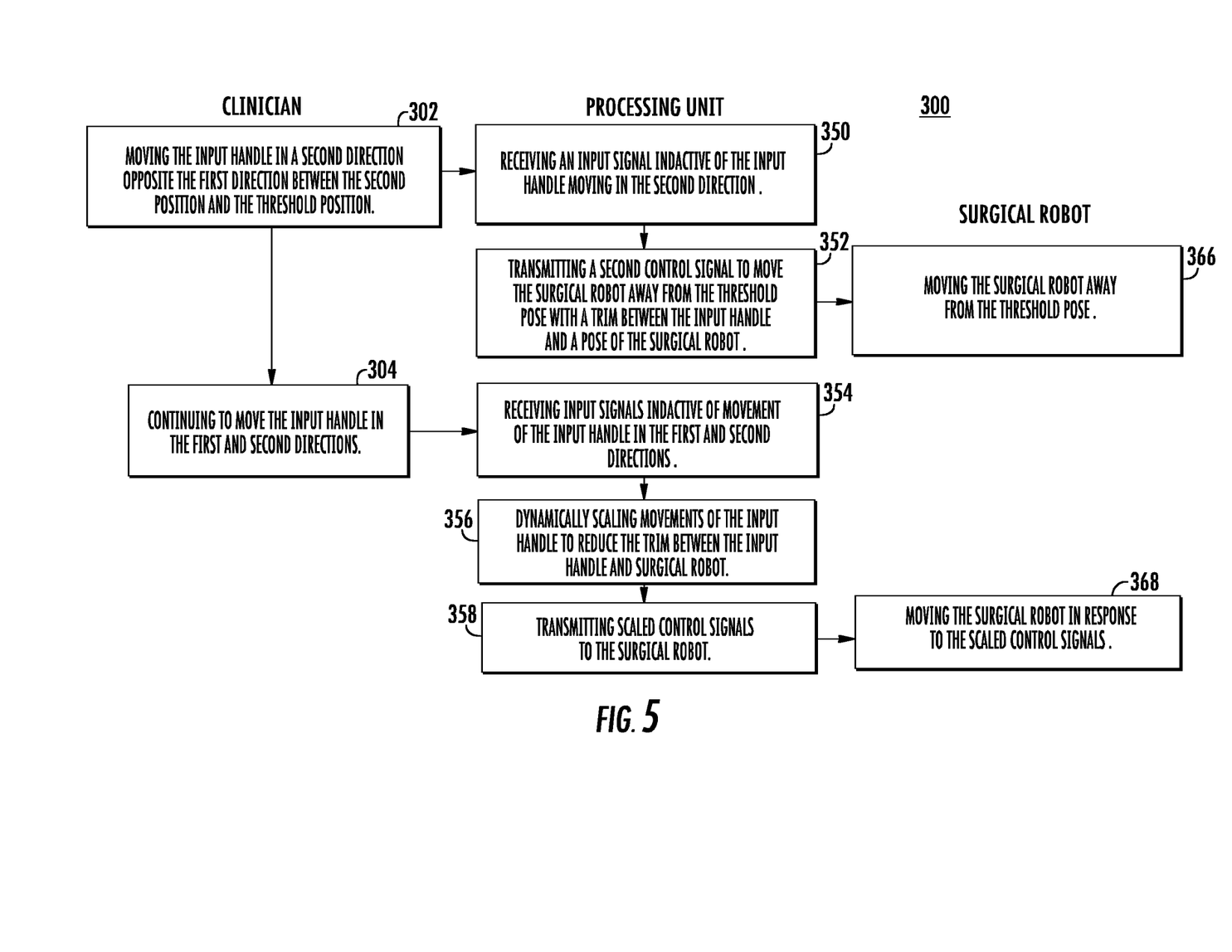
FIG. 5 is a flowchart of another method of collision handling and collision recovery in accordance with the present disclosure.

With additional reference to FIG. 5, another method 300 of collision recovery is disclosed in accordance with the present disclosure. After the processing unit 30 slips the position of the input handle 42 relative to the threshold pose of the surgical robot 10 to define an offset (Step 248), the input handle 42 is moved in the second direction along the control X axis (Step 302). The processing unit 30 receives an input signal indicative of the movement of the input handle 42 in the second direction (Step 350) and transmits a second control signal to the surgical robot 10 to move away from the threshold pose "T2" with a trim between the input handle and the pose of the surgical robot (Step 352). It will be appreciated that the trim is substantially equal to the offset between the threshold position "PT" and the second position "P2". The surgical robot 10 receives the second control signal and moves the surgical robot 10 away from the threshold pose (Step 366). The robotic surgical system 1 may continue to manipulate the surgical robot 10 in response to movements of the input handle 42 with the trim maintained between the position of the input handle 42 and the pose of the surgical robot 10.

Alternatively in some embodiments, the robotic surgical system 1 may dynamically scale the movement of the input handle 42 and the tool 20 to reduce or eliminate the trim in a manner imperceptible to a clinician. For example, the input handle 42 can be moved in the first and second directions along the control X axis such that input signals are transmitted to the processing unit 30 (Step 304). The processing unit 30 receives the input signals (Step 354) and dynamically scales movements of the input handle 42 to reduce the trim between the input handle 42 and the pose of the surgical robot 10 (Step 356). The processing unit 30 transmits scaled control signals to the surgical robot 10 (Step 358) which moves the surgical robot 10 in response to the scaled control signals (Step 368). The trim may be reduced to a predetermined value and the robotic surgical system 10 may continue to move the surgical robot 10 in response to movement of the input handle 42. In particular embodiments, the predetermined value of the trim is nonzero and in other embodiments the trim is reduced to zero such that the position of the input handle 42 corresponds to the pose of the surgical robot 10.

For a detailed discussion of a robotic surgical system functioning with an offset and/or dynamic scaling to eliminate an offset reference can be made to commonly owned U.S. Provisional Patent Application No. 62/554,292, filed Sep. 5, 2017 and entitled "ROBOTIC SURGICAL SYSTEMS WITH ROLL, PITCH, AND YAW REALIGNMENT INCLUDING TRIM AND FLIP ALGORITHMS", the entire contents of which are hereby incorporated by reference.

Slipping a position of the input handle 42 relative to a pose of the tool 20 allows for movement or repositioning of the input handle 42 within the workspace of the user interface 40 without movement of the tool 20 within the surgical site "S". The methods of collision recovery detailed above, e.g., moving the input handle 42 through a dead zone, operating with an offset, and dynamically scaling to eliminate offset, allows for predictable movement of a tool, e.g., tool 20, of a surgical robot after a collision. Such predictable movement may improve surgical outcomes, reduce the surgical time, reduce recovery time, and/or reduce the cost of surgery.

As detailed above, the user interface 40 is in operable communication with the surgical robot 10 to perform a surgical procedure on a patient; however, it is envisioned that the user interface 40 may be in operable communication with a surgical simulator (not shown) to virtually actuate a robotic system and/or tool in a simulated environment. For example, the robotic surgical system 1 may have a first mode in which the user interface 40 is coupled to actuate the surgical robot 10 and a second mode in which the user interface 40 is coupled to the surgical simulator to virtually actuate a robotic system. The surgical simulator may be a standalone unit or be integrated into the processing unit 30. The surgical simulator virtually responds to a clinician interfacing with the user interface 40 by providing visual, audible, force, and/or haptic feedback to a clinician through the user interface 40. For example, as a clinician interfaces with the input handles 42, the surgical simulator moves representative tools that are virtually acting on tissue. It is envisioned that the surgical simulator may allow a clinician to practice a surgical procedure before performing the surgical procedure on a patient. In addition, the surgical simulator may be used to train a clinician on a surgical procedure. Further, the surgical simulator may simulate "complications" during a proposed surgical procedure to permit a clinician to plan a surgical procedure.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A method of collision handling for a robotic surgical system, the method comprising:
    slipping an input handle of a user interface of the robotic surgical system relative to a pose of a tool of a surgical robot of the robotic surgical system when a portion of the surgical robot collides with an obstruction and the input handle is moved in a direction corresponding to moving the tool towards the obstruction, the input handle having an offset relative to a desired pose of the tool in response to slipping of the input handle; and
    slipping the input handle relative to the pose of the tool after the surgical robot reaches a predetermined force threshold to move the tool towards a desired pose.

2. The method according to claim 1, further comprising, in response to slipping the input handle, moving the input handle in a direction away from the obstruction such that the tool moves in a direction away from the obstruction maintaining a trim between a position of the input handle and a pose of the tool.

3. The method according to claim 2, further comprising the robotic surgical system providing force feedback to a clinician to resist slipping of the input handle beyond the threshold position.

4. The method according to claim 1, wherein the predetermined force threshold is non-zero.

5. The method according to claim 2, further comprising, in response to moving the input handle a distance corresponding to the offset, moving the tool in a direction away from the obstruction.

6. The method according to claim 2, wherein the trim is equal to the offset.

7. A method of collision handling for a robotic surgical system, the method comprising:
    slipping an input handle of a user interface of the robotic surgical system relative to a pose of a tool of a surgical robot of the robotic surgical system when a portion of the surgical robot collides with an obstruction and the input handle is moved in a direction corresponding to moving the tool towards the obstruction, the input handle having an offset relative to a desired pose of the tool in response to slipping of the input handle;
    in response to a moving of the input handle in a direction away from the obstruction, after the slipping the input handle, moving the tool in a direction away from the obstruction maintaining a trim between a position of the input handle and a pose of the tool; and
    dynamically scaling movement of the input handle relative to the pose of the tool in a direction parallel to the offset until the trim reaches a predetermined value.

8. The method according to claim 7, further comprising, in response to:
    moving the input handle in a direction to move the portion of the surgical robot away from the obstruction, after the slipping of the input handle; and
    moving the input handle a distance corresponding to the offset,
    moving the tool in a direction away from the obstruction.

9. The method according to claim 7, wherein the trim is equal to the offset.

10. The method according to claim 7, wherein the predetermined value is nonzero.

11. The method according to claim 7, wherein the dynamic scaling movement of the input handle relative to the post of the tool results in a reduction of the trim.

12. The method according to claim 11, wherein the reduction of the trim is in a manner imperceptible to the clinician.

13. A method of collision handling of a robotic surgical system with a processing unit of the robotic surgical system, the method comprising:
    receiving a first input signal from a user interface of the robotic surgical system to move a tool of a surgical robot of the robotic surgical system to a desired pose of the tool;
    transmitting an input control signal to the surgical robot to move the tool towards the desired pose;
    receiving a feedback signal from the surgical robot that a force to move the tool towards the desired pose is greater than a predetermined threshold;
    maintaining the tool at a threshold pose when the predetermined threshold is reached; and
    slipping a position of the input handle relative to the threshold pose to a second position of the input handle to define an offset between the second position of the input handle and a desired pose of the tool corresponding to the second position of the input handle.

14. The method according to claim 13, further comprising transmitting a feedback control signal to the user interface to resist movement of the input handle beyond a threshold position corresponding to the threshold pose of the tool.

15. The method according to claim 13, further comprising receiving a second input signal from the user interface after slipping the position of the input handle indicative of the input handle moving towards a threshold position corresponding to the threshold pose of the tool.

16. The method according to claim 15, further comprising maintaining the tool in the threshold pose in response to receiving the second input signal.

17. The method according to claim 15, further comprising transmitting a second control signal to the surgical robot to move the tool away from the desired pose with a trim defined between the input handle and the pose of the tool.

18. The method according to claim 17, wherein transmitting the second control signal includes the trim being equal to the offset between the second position of the input handle and the desired pose of the tool corresponding to the second position of the input handle.

19. The method according to claim 17, further comprising dynamically scaling movement of the input handle to the pose of the tool to reduce the trim between the position of the input handle and the pose of the tool until the trim reaches a predetermined value.

20. The method according to claim 19, wherein the predetermined value is nonzero.

* * * * *